(12) United States Patent
Chang et al.

(10) Patent No.: US 9,796,584 B2
(45) Date of Patent: Oct. 24, 2017

(54) METHOD FOR FABRICATING A MICRO-WELL OF A BIOSENSOR

(71) Applicant: Taiwan Semiconductor Manufacturing Co., Ltd., Hsin-Chu (TW)

(72) Inventors: Che-Ming Chang, Longtan Township (TW); Chih-Jen Chan, Changhua (TW); Chung-Yen Chou, Hsinchu (TW); Lee-Chuan Tseng, New Taipei (TW); Shih-Wei Lin, Taipei (TW); Yuan-Chih Hsieh, Hsinchu (TW)

(73) Assignee: Taiwan Semiconductor Manufacturing Co., Ltd., Hsin-Chu (TW)

( * ) Notice: Subject to any disclaimer, the term of this patent is extended or adjusted under 35 U.S.C. 154(b) by 0 days.

(21) Appl. No.: 15/436,938

(22) Filed: Feb. 20, 2017

(65) Prior Publication Data

US 2017/0158500 A1    Jun. 8, 2017

Related U.S. Application Data

(62) Division of application No. 14/645,788, filed on Mar. 12, 2015, now Pat. No. 9,606,081.

(51) Int. Cl.
*H01L 21/00* (2006.01)
*B81C 1/00* (2006.01)
(Continued)

(52) U.S. Cl.
CPC .... *B81C 1/00595* (2013.01); *B01L 3/502707* (2013.01); *B81B 1/002* (2013.01);
(Continued)

(58) Field of Classification Search
CPC  B81C 1/00595; G01N 27/4145; B81B 1/002; B81B 2207/07; B81B 2207/096;
(Continued)

(56) References Cited

U.S. PATENT DOCUMENTS

2010/0198521 A1*  8/2010  Haick ............... B82Y 15/00
                                                    702/19
2013/0200428 A1    8/2013  Rountree
(Continued)

OTHER PUBLICATIONS

Min, et al. "Selective Etching of HfO2 by Using Inductively-Coupled Ar/C4F8 Plasmas and the Removal of Etch Residue on Si by Using an O2 Plasma Treatment." Journal of the Korean Physical Society, vol. 53, No. 3, Sep. 2008, pp. 1675-1679.
(Continued)

*Primary Examiner* — Long K Tran
(74) *Attorney, Agent, or Firm* — Eschweiler & Potashnik, LLC (57) ABSTRACT

A bio-sensing semiconductor structure is provided. A transistor includes a channel region and a gate underlying the channel region. A first dielectric layer overlies the transistor. A first opening extends through the first dielectric layer to expose the channel region. A bio-sensing layer lines the first opening and covers an upper surface of the channel region. A second dielectric layer lines the first opening over the bio-sensing layer. A second opening within the first opening extends to the bio-sensing layer, through a region of the second dielectric layer overlying the channel region. A method for manufacturing the bio-sensing semiconductor structure is also provided.

20 Claims, 8 Drawing Sheets

(51) Int. Cl.
    *G01N 27/414*    (2006.01)
    *B81B 1/00*    (2006.01)
    *B01L 3/00*    (2006.01)
(52) U.S. Cl.
    CPC ...... *G01N 27/4145* (2013.01); *B01L 2200/10* (2013.01); *B01L 2300/0887* (2013.01); *B81B 2201/0214* (2013.01); *B81B 2207/07* (2013.01); *B81B 2207/096* (2013.01)
(58) Field of Classification Search
    CPC ....... B81B 2201/0214; B01L 3/502707; B01L 2200/10; B01L 2300/0887
    USPC ............................................ 257/253; 438/49
    See application file for complete search history.

(56) References Cited

U.S. PATENT DOCUMENTS

2013/0200438 A1* 8/2013 Liu ..................... G01N 27/414
                                                                257/253
2014/0308752 A1   10/2014 Chang

OTHER PUBLICATIONS

Notice of Allowance dated Nov. 10, 2016 in connection with U.S. Appl. No. 14/645,788.
Non-Final Office Action dated Jul. 14, 2016 in connection with U.S. Appl. No. 14/645,788.

* cited by examiner

METHOD FOR FABRICATING A MICRO-WELL OF A BIOSENSOR

REFERENCE TO RELATED APPLICATIONS

This Application is a Divisional of U.S. application Ser. No. 14/645,788, filed on Mar. 12, 2015, the contents of which are hereby incorporated by reference in its entirety.

BACKGROUND

Biosensors are devices for sensing and detecting analytes, and typically operate on the basis of one or more of electronic, chemical, optical, and mechanical detection principles. Detection can be performed by detecting the analytes themselves, or through interaction and reaction between reactants and the analytes. Biosensors are widely used in different life-science applications, ranging from environmental monitoring and basic life science research to Point-of-Care (PoC) in-vitro molecular diagnostics.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

The present disclosure provides many different embodiments, or examples, for implementing different features of this disclosure. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Moreover, "first", "second", "third", etc. may be used herein for ease of description to distinguish between different elements of a figure or a series of figures. "first", "second", "third", etc. are not intended to be descriptive of the corresponding element. Therefore, "a first dielectric layer" described in connection with a first figure may not necessarily corresponding to a "first dielectric layer" described in connection with another figure.

Some biosensors combine microelectromechanical systems (MEMS) technology with complementary-metal-oxide-semiconductor (CMOS) technology. These biosensors may include a CMOS device bonded to a carrier substrate through a front side of the CMOS device. A micro-well may be arranged over a transistor of the CMOS device within a dielectric layer arranged on a backside of the CMOS device. Further, a MEMS device may be arranged over the dielectric layer and bonded to the CMOS device through the backside of the CMOS device.

During the manufacture of the foregoing biosensors, the width of the micro-well immediately above a channel region of the transistor and the integrity of the channel region are critical for device performance. According to some methods, a single dry etch is performed into the dielectric layer to form the micro-well and to expose the channel region. However, these methods may damage a surface of the channel region and induce electrical failure. According to other methods, a dry etch is performed into the dielectric layer to form an opening. Thereafter, a wet etch is performed to expand the opening, thereby forming the micro-well and exposing the channel region. Advantageously, these other approaches may not damage the channel region. However, while these other methods may not damage the channel region, these other methods may enlarge the micro-well beyond the desired width and reduce the ability of the micro-well to trap desired analytes or carriers of the analytes.

In view of the foregoing, the present application is directed towards a method for manufacturing biosensors with improved control over the micro-well formation. Further, the present application is directed towards a biosensor and a semiconductor structure resulting from performance of the method. According to the method, a first opening is formed exposing a channel region of the transistor using a first, dry etch, followed by a second, wet etch. Thereafter, the first opening is lined by a bio-sensing layer and a dielectric layer overlying the bio-sensing layer. The bio-sensing layer is typically a high κ dielectric having a dielectric constant exceeding about 3.9. With the bio-sensing and dielectric layers formed, a third etch is performed through the dielectric layer to the bio-sensing layer to form a second opening with the critical width overlying the source/drain region.

Advantageously, by forming the micro-well according to the foregoing method, damage to the channel region may be prevented and control over the micro-well width is improved. For example, the width of the micro-well immediately above the channel region may be reduced from about 0.4 micrometers (μm) to about 0.2 μm. As another example, micro-wells failing to meet within wafer (WiW) and/or wafer to wafer (WtW) uniformity metrics may be reduced from about 59% to less than about 10%. The less than 10%, non-conforming micro-wells may be caused by oxide thickness variation and wet etchant lifetime. Further, the same photo mask may be used for the first, second, and third etches, so costs are minimally affected by the additional, third etch. Even more, etchants with a selectivity of about 20 for the dielectric layer, relative to the bio-sensing layer, are known, which may reduce over etching.

Figure 1:
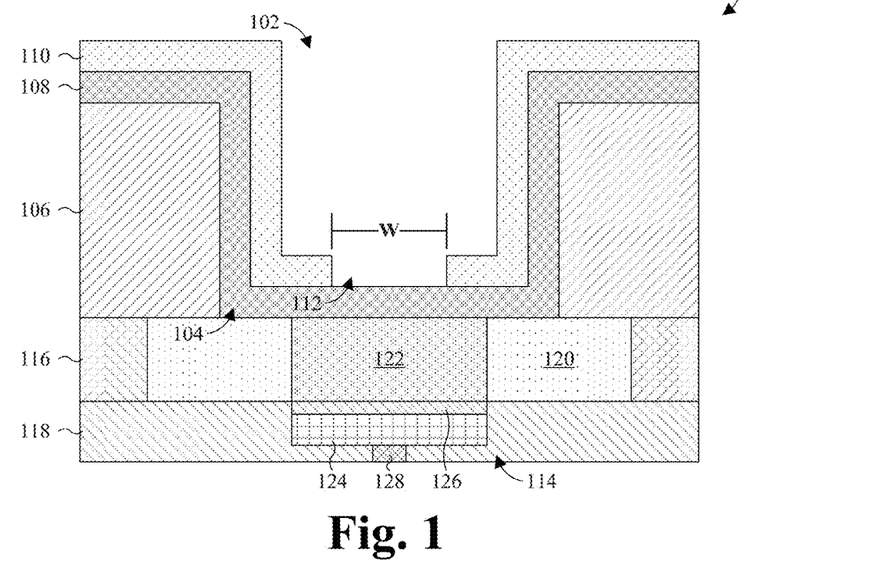
FIG. 1 illustrates a cross-sectional view of some embodiments of a semiconductor structure with a biosensor micro-well.

With reference to FIG. 1, a cross-sectional view 100 of some embodiments of a semiconductor structure with a biosensor micro-well 102 is provided. The biosensor micro-well 102 is arranged within a first opening 104 of a first dielectric layer 106 between sidewalls of a bio-sensing layer 108 and a second dielectric layer 110. The bio-sensing layer 108 extends along an upper surface of the first dielectric layer 106 and lines the first opening 104. The second dielectric layer 110 extends along the upper surface, and lines the first opening 104, over the bio-sensing layer 108. The first and second dielectric layers 106, 110 may be, for example, an oxide, such as silicon dioxide. Further, the first dielectric layer 106 may, for example, have a thickness of about 1 μm, and the second dielectric layer 110 may, for example, have a thickness of about 1000 Angstroms. The bio-sensing layer 108 may be, for example, a high κ dielectric, and/or may have, for example, a thickness of about 100 Angstroms. A high κ dielectric is a dielectric with a dielectric constant exceeding about 3.9, such as hafnium oxide (e.g., $HfO_2$).

A second opening 112, with a smaller footprint than the first opening 104, extends through the second dielectric layer 110 to the bio-sensing layer 108. In some embodiments, the second opening has a width W of about 0.2 to about 0.4 μm. As will be seen hereafter, during the formation of the second opening 112, the bio-sensing layer 108 serves as an etch stop layer. This prevents damage to the surface underlying the bio-sensing layer 108 and allows greater control over the width W of the second opening 112. As described above, the width W and the underlying surface integrity are critical for device performance.

A transistor 114 is arranged under the bio sensor micro-well 102 within a semiconductor layer 116 and a third, interlayer dielectric layer 118. The interlayer dielectric layer 118 is arranged under the first dielectric layer 106, and the semiconductor layer 116 is arranged over the interlayer dielectric layer 118 between the first and interlayer dielectric layers 106, 118. In some embodiments, the semiconductor layer 116 abuts the first dielectric layer 106 and/or the bio-sensing layer 108, and/or the interlayer dielectric layer 118 abuts the semiconductor layer 116. The interlayer dielectric layer 118 may be, for example, an oxide or a low κ dielectric. A low κ dielectric is a dielectric with a dielectric constant less than about 3.9. The semiconductor layer 116 may be, for example, silicon or some other semiconductor.

The transistor 114 includes a pair of source/drain regions 120, a channel region 122 extending between the source/drain regions 120, and a gate 124 arranged between the source/drain regions 120. The source/drain regions 120 are embedded within the semiconductor layer 116 and arranged on opposing sides of the gate 124. The gate 124 is arranged in the interlayer dielectric layer 118 and spaced from the semiconductor layer 116 by a gate dielectric layer 126 of the transistor 114. The gate dielectric layer 126 extends into the interlayer dielectric layer 118 from about even with an upper surface of the interlayer dielectric layer 118, and abuts the gate 124 within the interlayer dielectric layer 118. The gate 124 is electrically coupled with a BEOL metallization stack underlying the transistor 114 through a contact 128 arranged in the interlayer dielectric layer 118 and typically abutting the gate 124. The gate 124 and the contact 128 may be, for example, doped polysilicon or metal, such as tungsten or copper. The gate dielectric layer 126 may be, for example, an oxide.

During use of the micro-well 102, a test sample is applied to the micro-well 102, typically by micro fluidics. The test sample may include analytes suspended in a fluid and, in some embodiments, bound to carriers. To the extent that the test sample includes analytes, the analytes land on exposed regions of the bio-sensing layer 108. When analytes land on the bio-sensing layer 108, the amount of charge overlying the channel region 122 changes. For example, in some embodiments, when analytes land on the bio-sensing layer 108, a bio-reaction occurs between the bio-sensing layer 108 and the analytes to release ions and increase the pH in the micro-well 102. The increased pH thereafter induces a change in the amount of charge overlying the channel region 122.

The change in the amount of charge overlying the channel region 122 causes a change in the electrical characteristics of the transistor 114. By observing the electrical characteristics before and after the change in charge, the presence of analytes can be detected. For example, the threshold voltage $V_T$ of the transistor 114 may be increased by amount $\Delta V_T$ when analytes are present in the micro-well 102. By applying a voltage V that is greater than $V_T$, but less than $V_T + \Delta V_T$ to the gate 124, current will flow through the channel region 122 between the source/drain regions 120 depending upon whether analytes are present in the micro-well 102.

Figure 2:
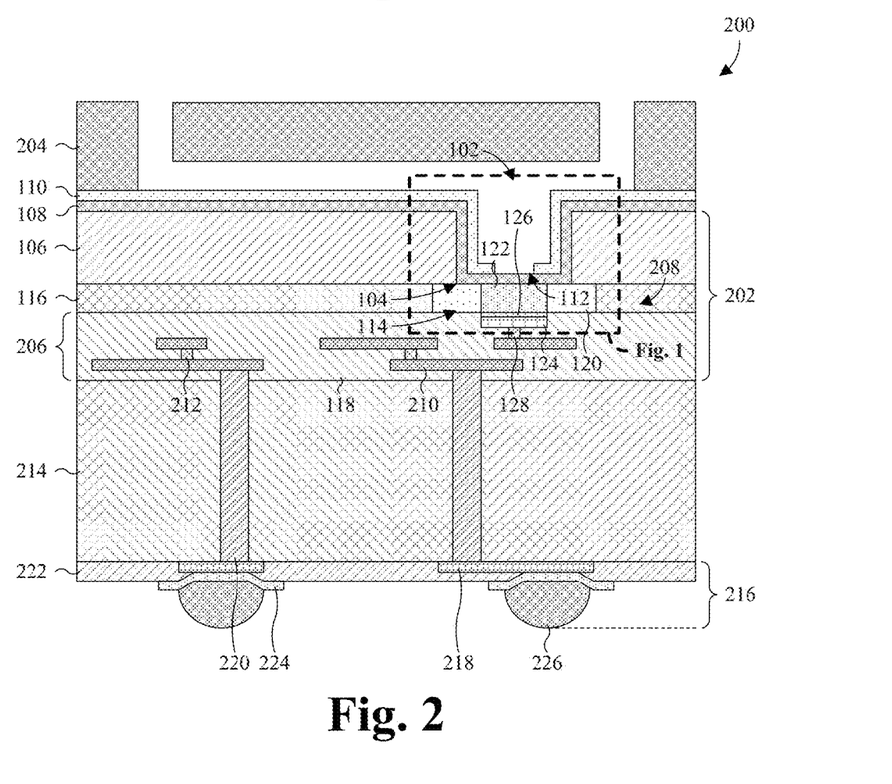
FIG. 2 illustrates a cross-sectional view of some embodiments of a biosensor with a micro-well.

With reference to FIG. 2, a cross-sectional view 200 of some embodiments of a biosensor with the micro-well 102 of FIG. 1 is provided. The micro-well 102 is arranged within a first opening 104 on a backside of an integrated circuit 202 between sidewalls of a bio-sensing layer 108 and a second dielectric layer 110. The bio-sensing layer 108 extends along the backside and lines the first opening 104. The second dielectric layer 110 extends along the backside, and lines the first opening 104, over the bio-sensing layer 108. A second opening 112, with a smaller footprint than the first opening 104, extends through the second dielectric layer 110 to the bio-sensing layer 108. The second dielectric layer 110 may be, for example, an oxide. The bio-sensing layer 108 may be, for example, a high κ dielectric. In some embodiments, a MEMS structure 204 is arranged over the integrated circuit 202 and the micro-well 102 to channel a test sample to the micro-well 102 through micro fluidics.

The integrated circuit 202 includes a first dielectric layer 106, a semiconductor layer 116 underlying the first dielectric layer 106, a BEOL metallization stack 206 underlying the semiconductor layer 116, and a device layer 208 arranged between the semiconductor layer 116 and the BEOL metallization stack 206. As will be seen hereafter, the first dielectric layer 106 and the semiconductor layer 116 may be the remnants of a silicon-on-insulator (SOI) substrate. The first dielectric layer 106 is arranged around the micro-well 102, and a transistor 114 of the device layer 208 is arranged under the micro-well 102.

The transistor 114 includes a pair of source/drain regions 120, a channel region 122 extending between the source/drain regions 120, and a gate 124 arranged between the source/drain regions 120 of the pair. The source/drain regions 120 are embedded within the semiconductor layer 116 and arranged on opposing sides of the gate 124. The gate 124 is arranged in a third, interlayer dielectric layer 118 of the BEOL metallization stack 206, and spaced from the semiconductor layer 116 by a fourth, gate dielectric layer 126 of the transistor 114. The gate dielectric layer 126 extends into the interlayer dielectric layer 118 and abuts the gate 124 within the interlayer dielectric layer 118. The gate 124 may be, for example, doped polysilicon or metal. The gate dielectric layer 126 may be, for example, an oxide.

The BEOL metallization stack 206 includes a plurality of metallization layers 210 stacked within the interlayer dielectric layer 118. One or more contacts 128 of the BEOL metallization stack 206 extend from an upper metallization layer to the device layer 208, including the gate 124 and/or the source/drain regions 120. Further, one or more first vias 212 of the BEOL metallization stack 206 extend between the metallization layers 210 to interconnect the metallization layers 210. The interlayer dielectric layer 118 may be, for example, a low κ dielectric or an oxide. The metallization layers 210, the contacts 128, and the first vias 212 may be, for example, a metal, such as copper or aluminum.

A carrier substrate 214 underlies the integrated circuit 202 between the integrated circuit 202 and a ball grid array (BGA) 216. The BGA 216 includes a redistribution layer (RDL) 218 arranged on a backside of the carrier substrate 214 and electrically coupled to the metallization layers 210 of the BEOL metallization stack 206 through one or more second, through substrate vias 220 extending through the carrier substrate 214. The RDL 218 is covered by a fifth, BGA dielectric layer 222, and under bump metallization (UBM) layers 224 extend through the BGA dielectric layer 222 to electrically couple solder balls 226 underlying the UBM layers 224 to the RDL 218. The BGA dielectric layer 222 may be, for example, an epoxy or a single mode fiber (SMF). The RDL 218, the UBM layers 224, the through substrate vias 220, and the solder balls 226 may be, for example, metals, such as copper, aluminum, and tungsten.

Figure 3:
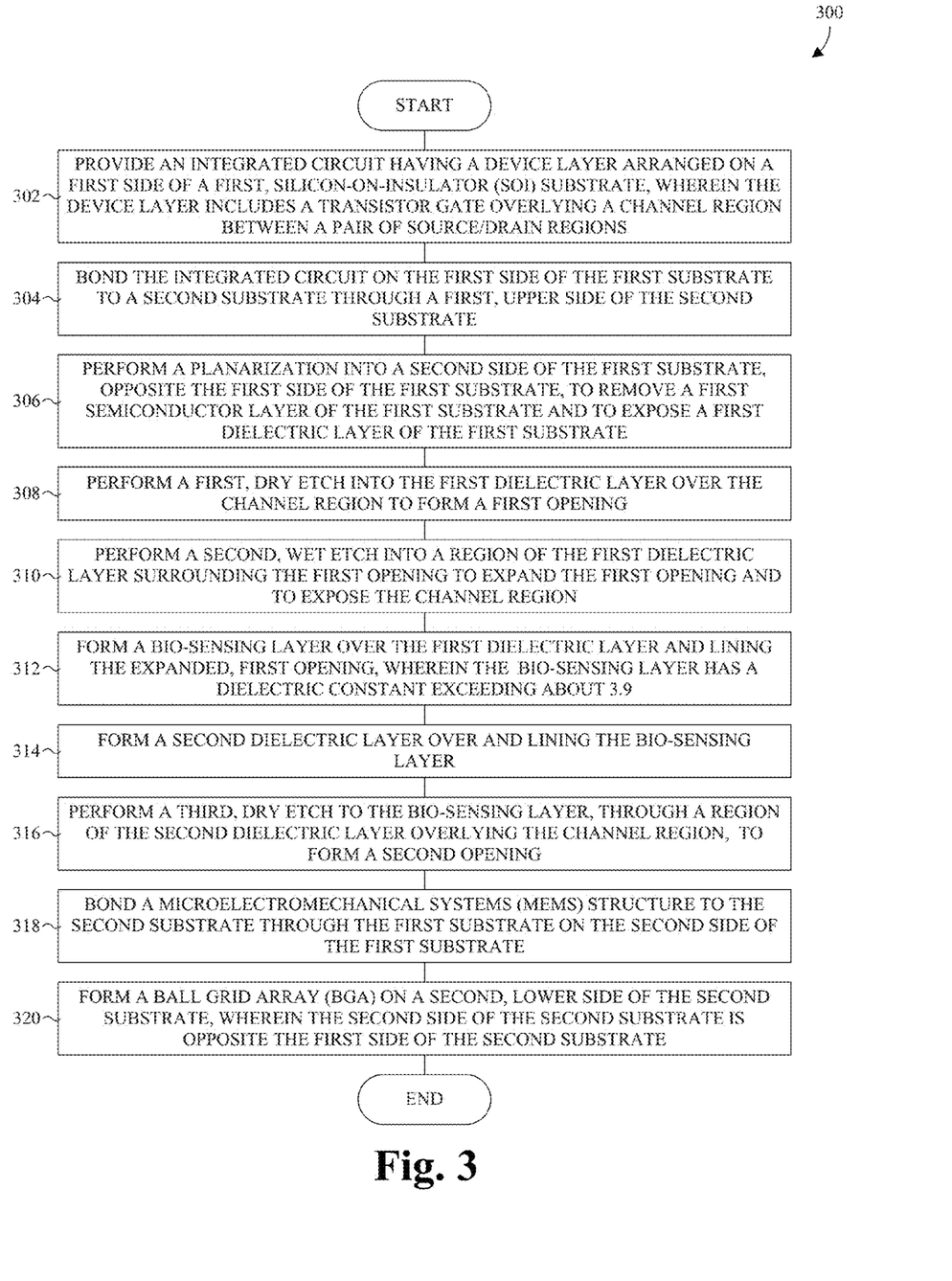
FIG. 3 illustrates a flowchart of some embodiments of a method for manufacturing a biosensor with a micro-well.

With reference to FIG. 3, a flowchart 300 of some embodiments of a method for manufacturing a biosensor with a micro-well is provided.

At 302, an integrated circuit having a device layer arranged on a first side of a first, SOI substrate is provided. The device layer includes a transistor gate overlying a channel region between a pair of source/drain regions.

At 304, the integrated circuit is bonded on the first side of the first substrate to a second substrate through a first, upper side of the second substrate.

At 306, a planarization is performed into a second side of the first substrate, opposite the first side of the first substrate, to remove a first semiconductor layer of the first substrate and to expose a first dielectric layer of the first substrate.

At 308, a first, dry etch is performed into the first dielectric layer over the channel region to form a first opening.

At 312, a second, wet etch is performed into a region of the first dielectric layer surrounding the first opening to expand the first opening and to expose the channel region.

At 314, a bio-sensing layer is formed over the first dielectric layer and lining the expanded, first opening. The bio-sensing layer has a dielectric constant exceeding about 3.9

At 316, a second dielectric layer is formed over and lining the bio-sensing layer.

At 318, a third, dry etch is performed to the bio-sensing layer, through a region of the second dielectric layer overlying the channel region, to form a second opening.

At 320, a MEMS structure is bonded to the second substrate through the first substrate on the second side of the first substrate.

At 322, a BGA is formed on a second, lower side of the second substrate, wherein the second side of the second substrate is opposite the first side of the second substrate.

Advantageously, by forming the micro-well with the additional, third etch, damage to the channel region is prevented and control over the micro-well width immediately above the channel region is improved. Further, the same mask may be used for the first, second, and third etches, so costs are minimally affected by the additional, third etch. Even more, etchants with a selectivity of about 20 for the second dielectric layer, relative to the bio-sensing layer, are known, which may reduce over etching.

While the method described by the flowchart 300 is illustrated and described herein as a series of acts or events, it will be appreciated that the illustrated ordering of such acts or events are not to be interpreted in a limiting sense. For example, some acts may occur in different orders and/or concurrently with other acts or events apart from those illustrated and/or described herein. Further, not all illustrated acts may be required to implement one or more aspects or embodiments of the description herein, and one or more of the acts depicted herein may be carried out in one or more separate acts and/or phases.

With reference to FIGS. 4-12, cross-sectional views of some embodiments of a biosensor at various stages of manufacture are provided to illustrate the method of FIG. 3. Although FIGS. 4-12 are described in relation to the method, it will be appreciated that the structures disclosed in FIGS. 4-12 are not limited to the method, but instead may stand alone as structures independent of the method. Similarly, although the method is described in relation to FIGS. 4-12, it will be appreciated that the method is not limited to the structures disclosed in FIGS. 4-12, but instead may stand alone independent of the structures disclosed in FIGS. 4-12.

Figure 4:
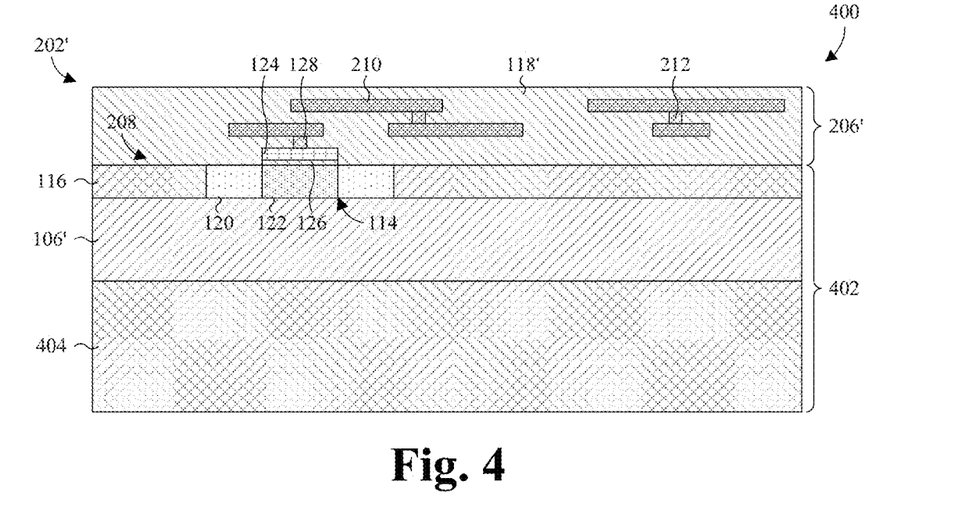
FIGS. 4-12 illustrate a series of cross-sectional views of some embodiments of a biosensor at various stages of manufacture, the biosensor having a micro-well.

FIG. 4 illustrates a cross-sectional view 400 of some embodiments corresponding to Act 302. As illustrated, an integrated circuit 202' is provided. The integrated circuit 202' includes a first substrate 402 including a carrier layer 404, a semiconductor layer 116, and a first dielectric layer 106' arranged between the semiconductor and carrier layers 116, 404. Typically, the first substrate 402 is an SOI substrate, but other types of substrate are amenable. The carrier and semiconductor layers 116, 404 may be, for example, silicon. The first dielectric layer 106' may be, for example, an oxide. Further, the first dielectric layer 106' may have, for example, a thickness of, for example, about 1 μm.

A device layer 208 having a transistor 114 is arranged over and within the second semiconductor layer 116. The transistor 114 includes a pair of source/drain regions 120, a channel region 122, a gate 124, and a second, gate dielectric layer 126. The source/drain regions 120 are embedded within the second semiconductor layer 116, and the channel region 122 is arranged in the second semiconductor layer 116 between the source/drain regions 120. Typically, the source/drain regions 120 have about the same thickness as the second semiconductor layer 116. The gate 124 is arranged over the second semiconductor layer 116 and the channel region 122 between the source/drain regions 120. Further, the gate 124 is spaced from the second semiconductor layer 116 and the channel region 122 by the second, gate dielectric layer 126. The gate 124 may be, for example, doped polysilicon or metal. The gate dielectric layer 126 may be, for example, an oxide.

A BEOL metallization stack 206' is arranged over the device layer 208 and the first substrate 402. The BEOL metallization stack 206' includes a plurality of metallization layers 210 stacked within a third, interlayer dielectric layer 118'. One or more contacts 128 of the BEOL metallization stack 206' extend from a lower metallization layer to the device layer 208, including the gate 124 and/or the source/ drain regions 120. Further, one or more first vias 212 of the BEOL metallization stack 206' extend between the metallization layers 210 to interconnect the metallization layers 210. The interlayer dielectric layer 118' may be, for example, a low κ dielectric or an oxide. The metallization layers 210, the contacts 128, and the first vias 212 may be, for example, a metal.

Figure 5:
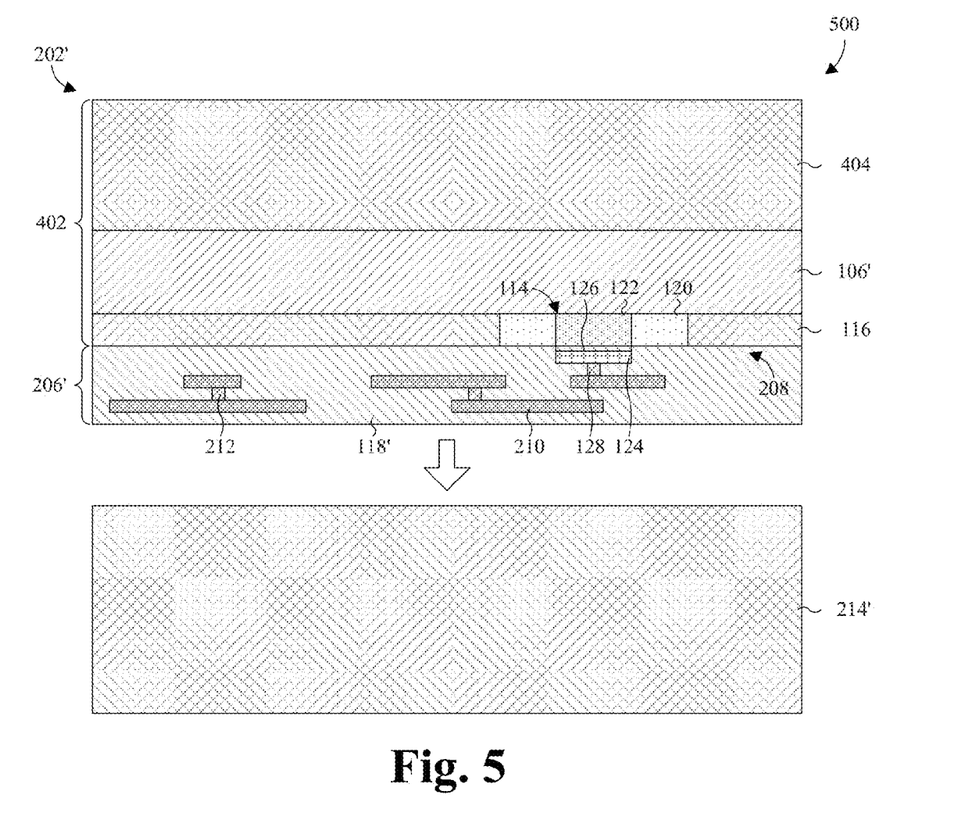

FIG. 5 illustrates a cross-sectional view 500 of some embodiments corresponding to Act 304. As illustrated, the integrated circuit 202' is rotated about 180 degrees about a horizontal axis and bonded to a second, carrier substrate 214' through a first, front side of the integrated circuit 202'. The integrated circuit 202' may be, for example, bonded to the carrier substrate 214' by a fusion bond or by using an adhesive. The carrier substrate 214' may be, for example, a bulk silicon substrate or an SOI substrate.

Figure 6:
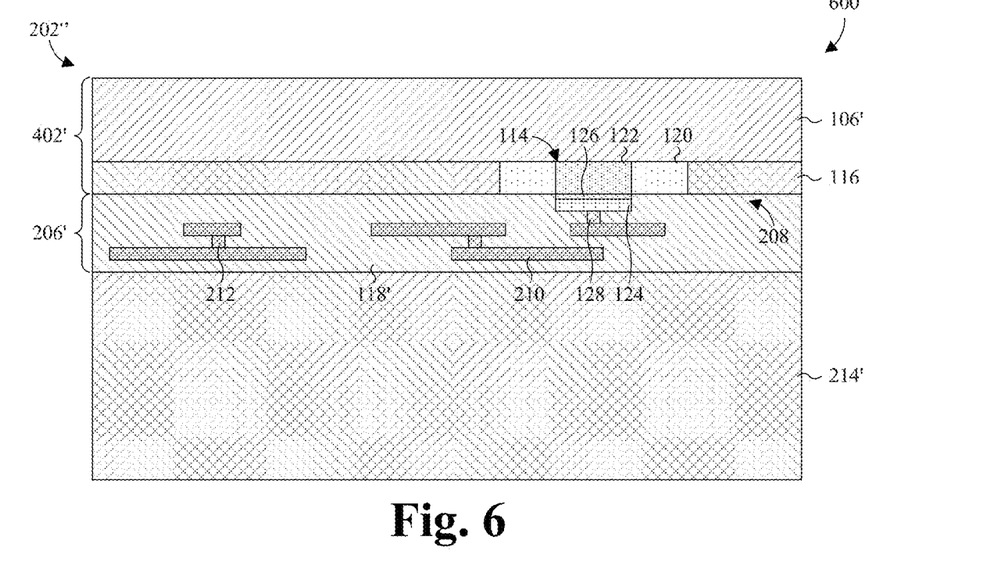

FIG. 6 illustrates a cross-sectional view 600 of some embodiments corresponding to Act 306. As illustrated, a planarization is performed into a second, backside of the integrated circuit 202', opposite the front side of the integrated circuit 202', to remove the carrier layer 404 and to expose the first dielectric layer 106'. The process for performing the planarization may include, for example, a chemical mechanical polishing (CMP).

FIGS. 4-6 are directed to embodiments in which the first substrate 402 includes carrier and semiconductor layers 116, 404 stacked on opposing sides of a dielectric layer 106'. It is to be appreciated, that in other embodiments, the first substrate 402 may be a bulk semiconductor substrate. In such embodiments the planarization of Act 306 may be unnecessary. Further, before proceeding further in the method of FIG. 3, a dielectric layer may be formed over the bulk semiconductor substrate to achieve a semiconductor structure similar to that shown in FIG. 6.

Figure 7:
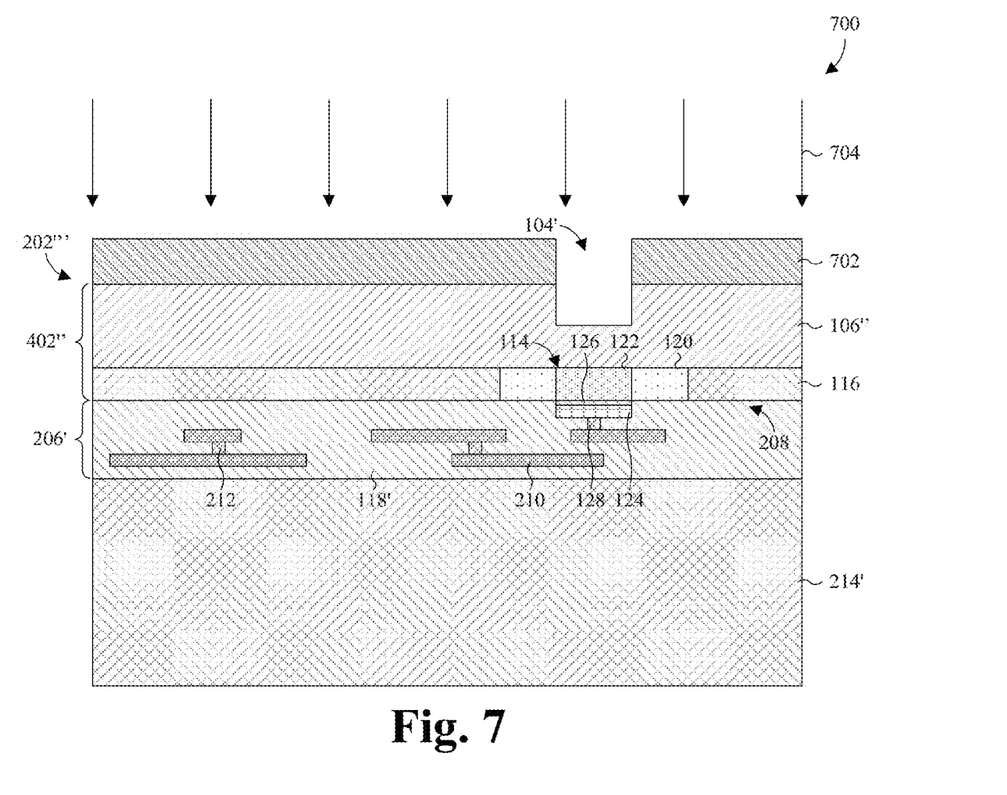

FIG. 7 illustrates a cross-sectional view 700 of some embodiments corresponding to Act 308. As illustrated, a first, dry etch is performed into the backside of the remaining integrated circuit 202'' and the remaining first substrate 402' to form a first opening 104' over the channel region 122. In other words, the first etch is performed into the first dielectric layer 106' to form the first opening 104' over the channel region 122. The first etch is typically anistropic and does not extend completely through the first dielectric layer 106'. In some embodiments, the process for performing the first etch includes forming a first photoresist layer 702 masking regions of the first dielectric layer 106' surrounding the first opening 104'. Thereafter, a dry etchant 704 is applied to the first dielectric layer 106' according to the first photoresist layer 702. The dry etchant may have a base gas of, for example, argon (Ar), tetrafluoromethane ($CF_4$), fluoroform ($CHF_3$), or sulfur hexafluoride ($SF_6$). In other embodiments, a wet etch or some other etch is performed in lieu of the dry etch.

Figure 8:
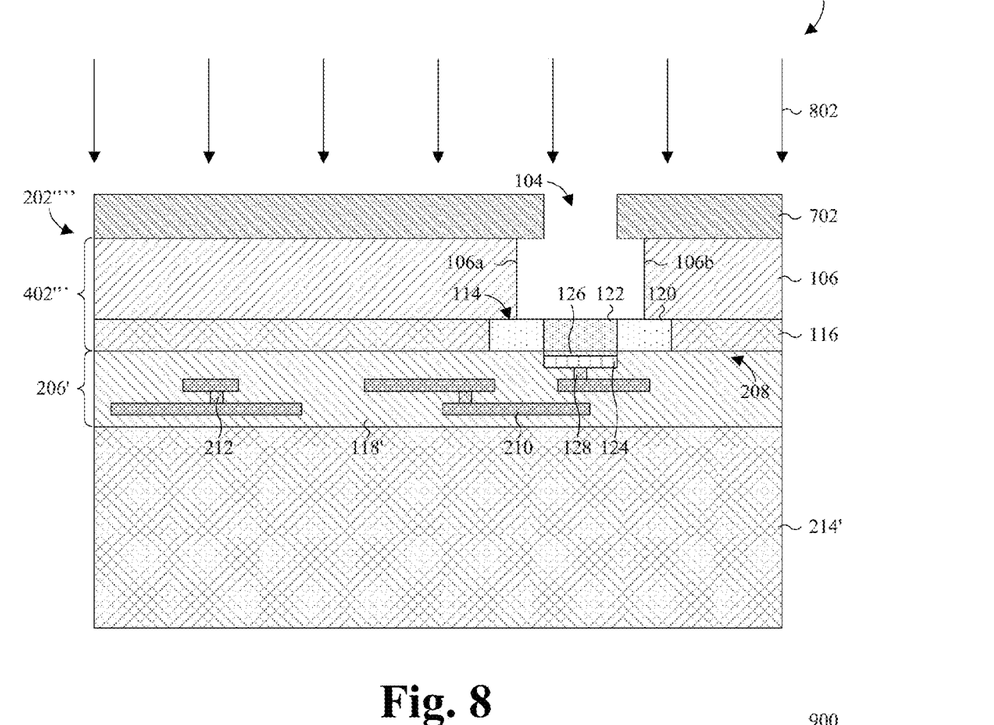

FIG. 8 illustrates a cross-sectional view 800 of some embodiments corresponding to Act 310. As illustrated, a second, wet etch is performed into the backside of the remaining first substrate 402'', the remaining integrated circuit 202', and a region of the remaining first dielectric layer 106'' extending along the first opening 104'. The second etch is typically isotropic and expands the first opening 104' to expose the channel region 122. The second etch may result in rounded and/or tilted sidewalls, although vertical sidewalls 106a, 106b are illustrated. In some embodiments, the process for performing the second etch includes applying a wet etchant 802 to the remaining first dielectric layer 106'' with the first photoresist layer 702 in place. The first photoresist layer 702 is then removed. The wet etchant 802 may be, for example, a buffered oxide etchant (BOE). In other embodiments, a dry etch or some other etch is performed in lieu of the wet etch.

Figure 9:
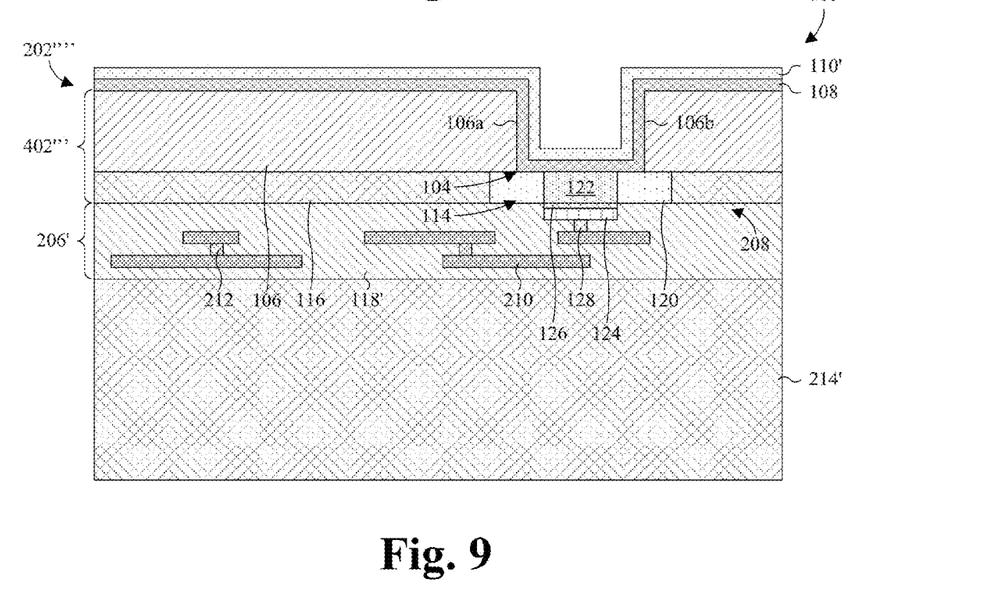

FIG. 9 illustrates a cross-sectional view 900 of some embodiments corresponding to Acts 312 and 314. As illustrated, a bio-sensing layer 108 is formed conformally extending along the backside of the remaining first substrate 402''', the remaining integrated circuit 202'''', and the remaining first dielectric layer 106, and lining the first, expanded opening 104. The bio-sensing layer 108 is formed as a high κ dielectric with a dielectric constant exceeding about 3.9. For example, the bio-sensing layer 108 may be formed as hafnium oxide. Further, in some embodiments, the bio-sensing layer 108 is formed with a thickness of about 100 Angstroms. The process for forming the bio-sensing layer 108 may include, for example, chemical vapor deposition (CVD), physical vapor deposition (PVD), atomic layer deposition (ALD), or some other deposition technique.

Also illustrated by FIG. 9, a third dielectric layer 110' is formed conformally extending along the backside of the remaining first dielectric layer 106, and lining the first, expanded opening 104 over the bio-sensing layer 108. The third dielectric layer 110' may be, for example, formed as an oxide. Further, the third dielectric layer 110' may be, for example, formed with a thickness of about 1000 Angstroms. The process for forming the third dielectric layer 110' may include, for example, CVD, PVD, or ALD. Thus, in some embodiments, the bio-sensing layer 108 and the third dielectric layer 110' may exhibit a v-shaped or u-shaped cross-sectional profile.

Figure 10:
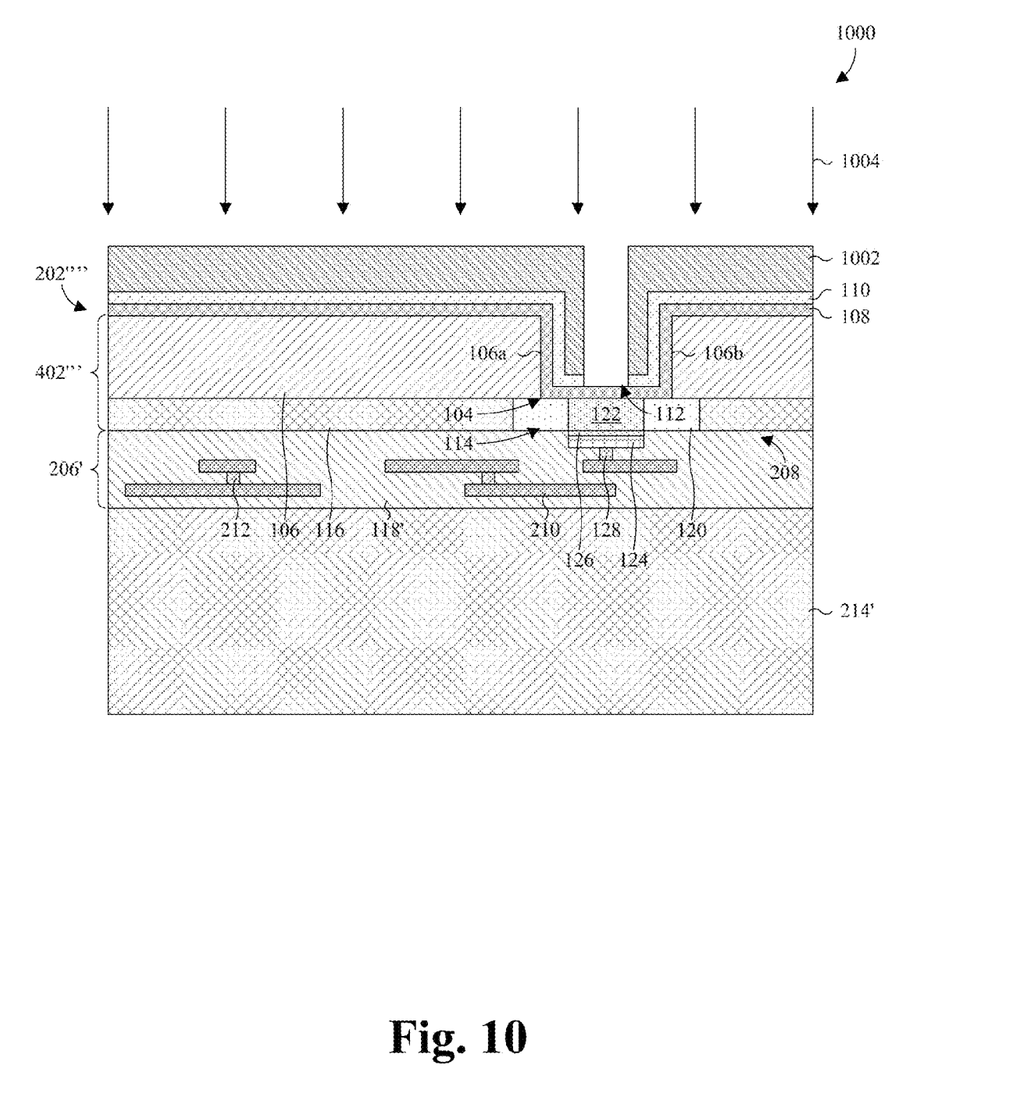

FIG. 10 illustrates a cross-sectional view 1000 of some embodiments corresponding to Act 316. As illustrated, a third, dry etch is performed to the bio-sensing layer 108, through a region of the third dielectric layer 110' overlying the channel region 122, to form a second opening 112. In some embodiments, the second opening 112 is formed with a width of about 0.2 μm to about 0.4 μm. The third etch is typically anistropic and exposes a region of the bio-sensing layer 108 immediately above the channel region 122. Advantageously, during the third etch, the bio-sensing layer 108 serves as an etch stop to prevent surface damage to the channel region 122 and to allow increased control over the width of the second opening 112. As discussed above, by preventing surface damage and increasing control over the second opening width, device performance is increased.

In some embodiments, the process for performing the third etch includes forming a second photoresist layer 1002 masking regions of the third dielectric layer 110' surrounding the second opening 112. Advantageously, the same photomask used to form the first photoresist layer 702 may be used to form the second photoresist layer 1002, thereby reducing costs. Thereafter, a dry etchant 1004 is applied to the third dielectric layer 110' according to the second photoresist layer 1002. The dry etchant 1004 may have a base gas of, for example, Ar, $CF_4$, $CHF_3$, or $SF_6$. In some embodiments, the dry etchant 1004 has a selectivity of about 20 for the third dielectric layer 110' relative to the bio-sensing layer 108. For example, such a selectivity may be obtained by applying the dry etchant 1004 from about 60 inches above the third dielectric layer 110' with a pressure of about 800 millitorr and a power of about 800 watts, where the dry etchant 1004 includes about 100 standard cubic centimeters per minute (sccm) of Ar, about 350 sccm of helium (He), about 50 sccm of $CF_4$, about 30 sccm of $CHF_3$, and about 20 sccm of nitrogen ($N_2$). With the dry etchant 1004 applied, the second photoresist layer 1002 is removed.

In other embodiments, a wet etch or some other etch is performed in lieu of the dry etch.

Figure 11:
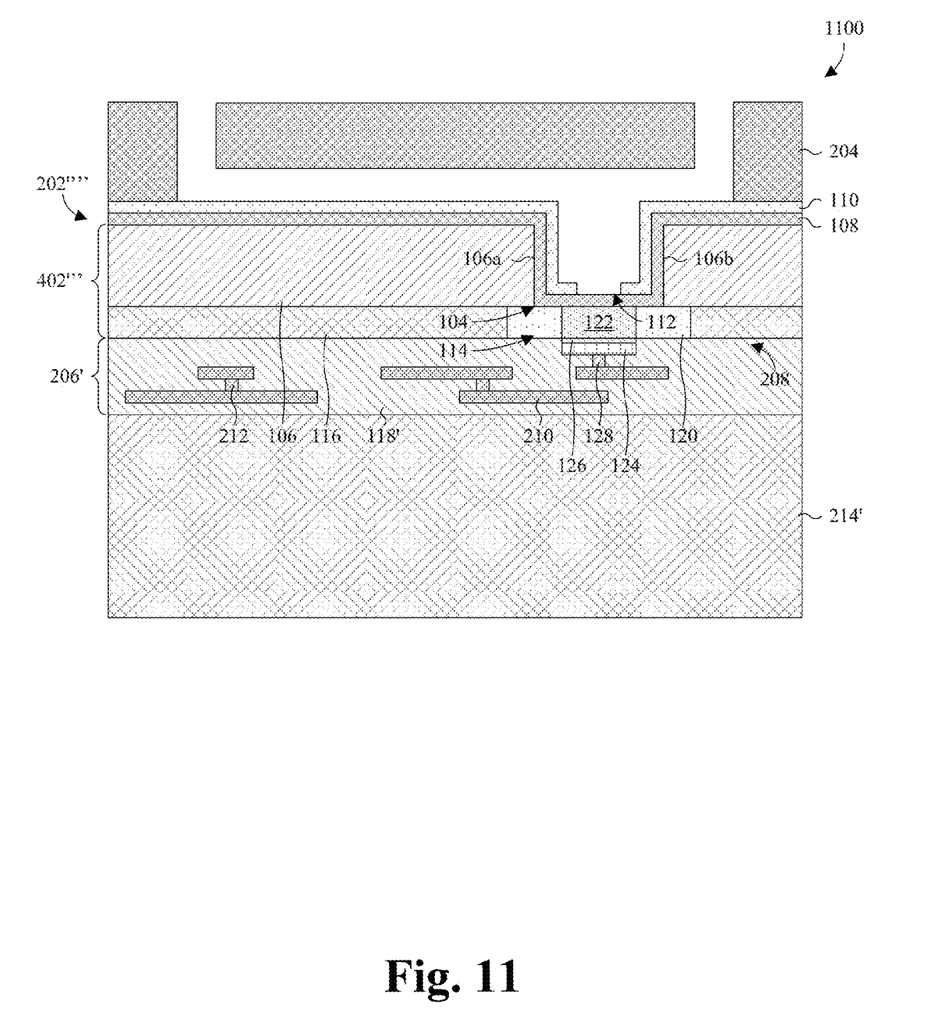

FIG. 11 illustrates a cross-sectional view 1100 of some embodiments corresponding to Act 318. As illustrated, a MEMS structure 204 is bonded to the second substrate 214' through the remaining integrated circuit 202''''. The MEMS structure 204 uses micro fluidics to direct a test sample to the first, expanded and second openings 104, 112. In other embodiments, the MEMS structure 204 may be arranged on the backside of the second substrate 214'.

Figure 12:
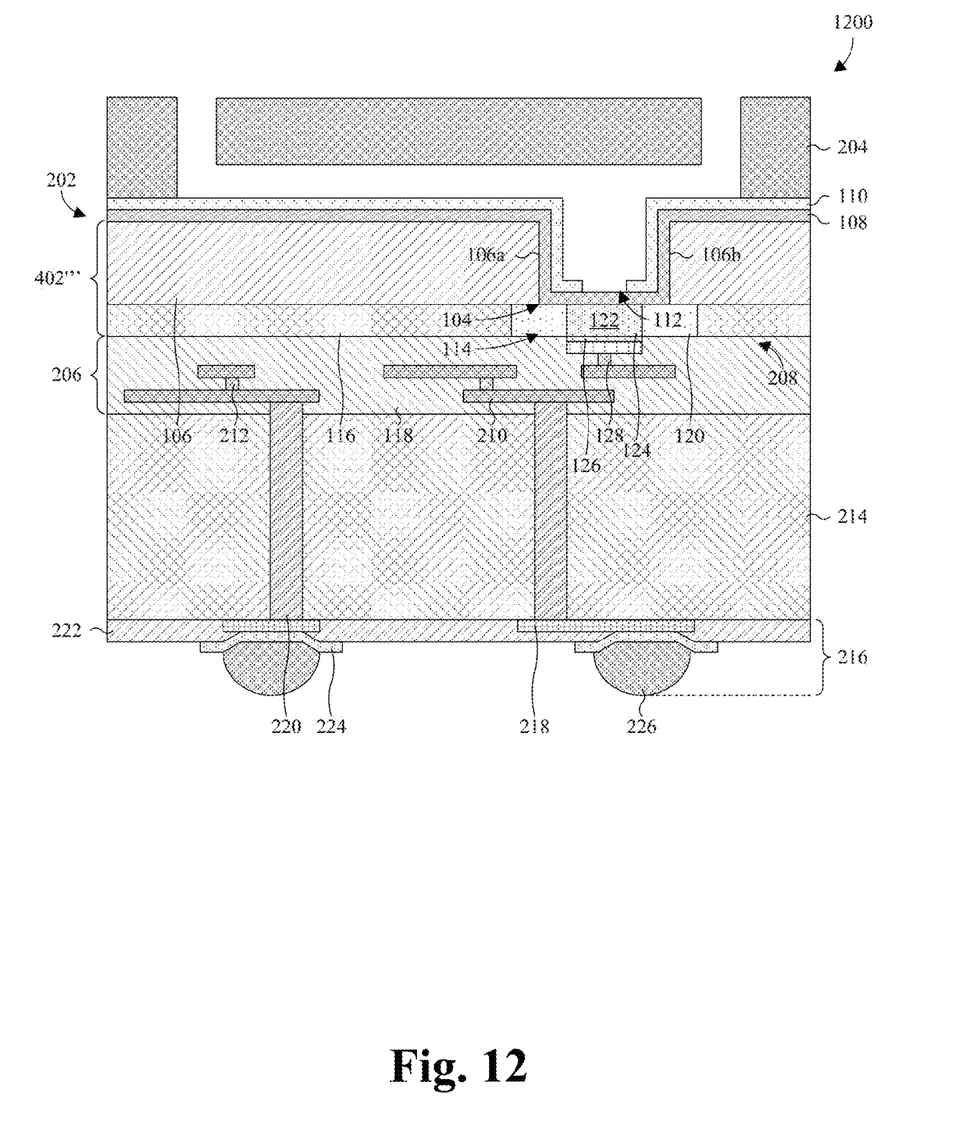

FIG. 12 illustrates a cross-sectional view 1200 of some embodiments corresponding to Act 320. As illustrated, one or more second, through substrate vias 220 extending through the second substrate 214' to the metallization layers 210 are formed. Also illustrated, a BGA 216 is formed on the backside of the second substrate 214'. The BGA 216 includes a RDL 218 electrically coupled to the metallization layers 210 through the second vias 220. The RDL 218 is covered by a fourth, BGA dielectric layer 222, and UBM layers 224 extend through the BGA dielectric layer 222 to electrically couple solder balls 226 underlying the UBM layers 224 to the RDL 218. In other embodiments, schemes other than the BGA 216 can be used for packaging the semiconductor structure.

Thus, in some embodiments, the present disclosure provides a bio-sensing semiconductor structure. A transistor includes a channel region and a gate underlying the channel region. A first dielectric layer overlies the transistor. A first opening extends through the first dielectric layer to expose the channel region. A bio-sensing layer lines the first opening and covers an upper surface of the channel region. A second dielectric layer lines the first opening over the bio-sensing layer. A second opening within the first opening extends to the bio-sensing layer, through a region of the second dielectric layer overlying the channel region.

In other embodiments, the present disclosure provides a method for manufacturing a bio-sensing semiconductor structure. A semiconductor structure in which a first dielectric layer overlies a transistor is provided. The transistor includes a channel region overlying a gate. A first etch is performed into the first dielectric layer to form a first opening overlying the channel region. A second etch is performed into a region of the first dielectric layer extending along the first opening to expand the first opening and to expose the channel region. A bio-sensing layer is formed lining the first, expanded opening. A second dielectric layer is formed lining the first, expanded opening over the bio-sensing layer. A third etch is performed to the bio-sensing layer, through a region of the second dielectric layer overlying the channel region, to form a second opening.

In yet other embodiments, the present disclosure provides a bio-sensing semiconductor structure. ABEOL metallization stack overlies a substrate and includes a gate electrode near an upper surface thereof. A semiconductor layer overlies the BEOL metallization stack and includes first and second source/drain regions which are spaced apart from one another by a channel region. The channel region overlies the gate electrode and is separated therefrom by a gate dielectric. A first dielectric layer overlies the semiconductor layer and includes a first opening therein. The first opening is configured to retain a liquid test sample for bio-sensing analysis and is disposed directly over the channel region. A bio-sensing layer lines the well recess, covers inner sidewalls of the first dielectric layer proximate to the channel region, and covers an upper surface of the channel region. A second dielectric layer overlies the bio-sensing layer and has a second opening that exposes less than an entire upper surface of the bio-sensing layer within the first opening.

In yet other embodiments, the present disclosure provides a semiconductor structure. A semiconductor substrate comprises a pair of source/drain regions and a channel region. The channel region is between the source/drain regions. The source/drain and channel regions each extend from a bottom surface of the semiconductor substrate to a top surface of the semiconductor substrate. A transistor comprises the source/drain regions, the channel region, and a gate electrode. The gate electrode is directly under the channel region. A first dielectric layer covers the semiconductor substrate. The first dielectric layer comprises a first well opening covering the channel region. A bio-sensing layer conformally lines and contacts sidewalls of the first well opening defined by the first dielectric layer, and further conformally lines and contacts a bottom surface of the first well opening defined by the semiconductor substrate. The bio-sensing layer is a different material than the first dielectric layer. A second dielectric layer conformally lines and contacts the bio-sensing layer. The second dielectric layer lines the sidewalls of the first well opening over the bio-sensing layer, and further lines the bottom surface of the first well opening over the bio-sensing layer. A segment of the second dielectric layer lining the bottom surface of the first well opening comprises a second well opening over and exposing the bio-sensing layer. The second dielectric layer is a different material than the bio-sensing layer.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A bio-sensing semiconductor structure comprising:
   a transistor comprising a channel region and a gate underlying the channel region;
   a first dielectric layer overlying the transistor;
   a first opening extending through the first dielectric layer to expose the channel region;
   a bio-sensing layer lining the first opening and covering an upper surface of the channel region;
   a second dielectric layer lining the first opening over the bio-sensing layer; and
   a second opening within the first opening that extends to the bio-sensing layer, through a region of the second dielectric layer overlying the channel region.

2. The bio-sensing semiconductor structure according to claim 1, wherein the bio-sensing layer has a dielectric constant exceeding about 3.9.

3. The bio-sensing semiconductor structure according to claim 1, wherein the bio-sensing layer includes hafnium oxide.

4. The bio-sensing semiconductor structure according to claim 1, wherein the bio-sensing layer and the second dielectric layer respectively have thicknesses of about 100 angstroms (Å) and about 1000 Å.

5. The bio-sensing semiconductor structure according to claim 1, wherein the second opening has a width of about 0.2 micrometers (μm) to about 0.4 μm.

6. The bio-sensing semiconductor structure according to claim 1, further including:
a semiconductor layer underlying the first dielectric layer, wherein the channel region is arranged within the semiconductor layer between a pair of source/drain regions of the transistor; and
a third dielectric layer underlying the semiconductor layer, wherein the gate is arranged within the third dielectric layer and spaced from the channel region by a fourth dielectric layer of the transistor.

7. The bio-sensing semiconductor structure according to claim 6, wherein the bio-sensing layer and second dielectric layer each have a u-shaped or v-shaped cross-sectional profile.

8. The bio-sensing semiconductor structure according to claim 1, further including:
a microelectromechanical systems (MEMS) structure arranged over the first dielectric layer and configured to channel a test sample to the second opening using micro fluidics.

9. The bio-sensing semiconductor structure according to claim 1, further including:
a back-end-of-line (BEOL) metallization stack underlying the transistor, wherein the BEOL metallization stack includes a plurality of metallization layers stacked within a third dielectric layer and electrically coupled to the gate by a contact.

10. A bio-sensing semiconductor structure comprising:
a substrate;
a back-end-of-line (BEOL) metallization stack overlying the substrate and including a gate electrode near an upper surface thereof;
a semiconductor layer overlying the BEOL metallization stack and including first and second source/drain regions which are spaced apart from one another by a channel region, wherein the channel region overlies the gate electrode and is separated therefrom by a gate dielectric layer;
a first dielectric layer overlying the semiconductor layer and including a first opening therein, wherein the first opening is configured to retain a liquid test sample for bio-sensing analysis and is disposed directly over the channel region;
a bio-sensing layer lining the first opening, covering inner sidewalls of the first dielectric layer proximate to the channel region, and covering an upper surface of the channel region; and
a second dielectric layer overlying the bio-sensing layer and having a second opening that exposes less than an entire upper surface of the bio-sensing layer within the first opening.

11. The bio-sensing semiconductor structure according to claim 10, wherein opposite sidewalls of the second opening are defined by the second dielectric layer and are laterally spaced between the first and second source/drain region.

12. The bio-sensing semiconductor structure according to claim 10, wherein the bio-sensing layer is a different material than the first dielectric layer and the second dielectric layer.

13. The bio-sensing semiconductor structure according to claim 12, wherein the bio-sensing layer is hafnium oxide, and wherein the first and second dielectric layers are silicon dioxide.

14. The bio-sensing semiconductor structure according to claim 10, wherein the BEOL metallization stack comprises an interlayer dielectric layer, a plurality of metallization layers, a via layer, and a contact layer, wherein the via layer is between the metallization layers, wherein the contact layer is between a first metallization layer of the BEOL metallization stack and the semiconductor layer, and wherein the contact layer extends from contact with the gate electrode to contact with the first metallization layer.

15. The bio-sensing semiconductor structure according to claim 14, further comprising:
a through substrate via (TSV) extending through the substrate, from contact with a last metallization layer of the BEOL metallization stack to a bottom surface of the substrate, wherein the first metallization layer is a closest one of the metallization layers to the semiconductor layer, and wherein the last metallization layer is a farthest one of the metallization layers from the semiconductor layer.

16. The bio-sensing semiconductor structure according to claim 10, wherein the bio-sensing layer covers a top surface of the first dielectric layer, wherein the second dielectric layer covers the bio-sensing layer outside the first opening, and wherein the bio-sensing semiconductor structure further comprises:
a microelectromechanical systems (MEMS) structure arranged over the second dielectric layer and configured to channel a test sample to the first and second openings using micro fluidics, wherein the MEMS structure contacts the second dielectric layer on opposite sides of the first opening.

17. The bio-sensing semiconductor structure according to claim 10, wherein the bio-sensing layer conformally lines the first opening, and wherein the second dielectric layer conformally lines the first opening over the bio-sensing layer.

18. The bio-sensing semiconductor structure according to claim 10, wherein the source/drain regions extend continuously from a bottom surface of the semiconductor layer to a top surface of the semiconductor layer.

19. A semiconductor structure comprising:
a semiconductor substrate comprising a pair of source/drain regions and a channel region, wherein the channel region is between the source/drain regions, and wherein the source/drain and channel regions each extend from a bottom surface of the semiconductor substrate to a top surface of the semiconductor substrate;
a transistor comprising the source/drain regions, the channel region, and a gate electrode, wherein the gate electrode is directly under the channel region;
a first dielectric layer covering the semiconductor substrate, wherein the first dielectric layer comprises a first well opening covering the channel region;
a bio-sensing layer conformally lining and contacting sidewalls of the first well opening defined by the first dielectric layer, and further conformally lining and contacting a bottom surface of the first well opening defined by the semiconductor substrate, wherein the bio-sensing layer is a different material than the first dielectric layer; and
a second dielectric layer conformally lining and contacting the bio-sensing layer, wherein the second dielectric layer lines the sidewalls of the first well opening over the bio-sensing layer, and further lines the bottom surface of the first well opening over the bio-sensing layer, wherein a segment of the second dielectric layer lining the bottom surface of the first well opening comprises a second well opening over and exposing the bio-sensing layer, and wherein the second dielectric layer is a different material than the bio-sensing layer.

20. The semiconductor structure according to claim 19, further comprising:
- a second semiconductor substrate;
- an interconnect structure covering the second semiconductor substrate, and comprising an interlayer dielectric layer, metallization layers, a via layer, and a contact layer, wherein the via layer is between the metallization layers, and wherein the contact layer is between a first metallization layer of the interconnect structure and the semiconductor substrate; and
- a through substrate via extending from contact with a last metallization layer of the interconnect structure to a bottom surface of the second semiconductor substrate, wherein the first metallization layer and the last metallization layer are respectively a closest one of the metallization layers to the semiconductor substrate and a farthest one of the metallization layers from the semiconductor substrate;
- wherein the semiconductor substrate covers the interconnect structure, wherein the gate electrode is between the interconnect structure and the semiconductor substrate, and wherein the contact layer extends from contact with the gate electrode to contact with the first metallization layer.

* * * * *